United States Patent [19]

Sungaila

[11] Patent Number: 4,831,846
[45] Date of Patent: May 23, 1989

[54] LOW TEMPERATURE CRYOPROBE

[75] Inventor: Zenon F. Sungaila, Orland Park, Ill.

[73] Assignee: The United States of America as represented by the United States Department of Energy, Washington, D.C.

[21] Appl. No.: 180,502

[22] Filed: Apr. 12, 1988

[51] Int. Cl.[4] .............................................. F25B 19/00
[52] U.S. Cl. ..................................... 62/51.3; 62/52.1; 62/293; 128/303.1
[58] Field of Search ...................... 62/514 R, 293, 52; 128/303.1

[56] References Cited

U.S. PATENT DOCUMENTS

| 2,223,152 | 11/1940 | Nagin | 62/399 |
|---|---|---|---|
| 2,241,186 | 5/1941 | Coons | 62/399 |
| 3,146,608 | 9/1964 | Carpenter | 62/293 |
| 3,502,081 | 3/1970 | Amoils | 62/293 |
| 3,628,347 | 12/1971 | Puckett et al. | 62/399 |
| 3,662,561 | 5/1972 | Schroeder | 62/52 |
| 3,667,248 | 6/1972 | Carlson | 62/293 |
| 3,696,636 | 10/1972 | Mille | 62/399 |
| 3,794,039 | 2/1974 | Kollner et al. | 62/293 |
| 3,807,403 | 4/1974 | Stumpf et al. | 62/293 |
| 3,971,383 | 7/1976 | van Gerven | 62/293 |
| 4,074,717 | 2/1978 | Schuylze et al. | 128/303.1 |
| 4,116,199 | 9/1978 | Byrne | 220/901 |
| 4,146,030 | 3/1979 | Holroyd | 62/293 |
| 4,206,760 | 6/1980 | Davis | 62/293 |
| 4,211,231 | 7/1980 | Rzasa | 62/293 |
| 4,213,501 | 7/1980 | Pfeiffer et al. | 62/52 |
| 4,236,518 | 12/1980 | Floyd | 128/303.1 |
| 4,291,541 | 9/1981 | Kneip, Jr. et al. | 220/901 |
| 4,376,376 | 3/1983 | Gregory | 62/51 |

Primary Examiner—Ronald C. Capossela
Attorney, Agent, or Firm—Helen S. Cordell; John M. Albrecht; Judson R. Hightower

[57] ABSTRACT

A portable, hand held probe usable within a small confine to produce a point source of nitrogen or helium at a relatively constant temperature of 77 degrees Kelvin.

9 Claims, 1 Drawing Sheet

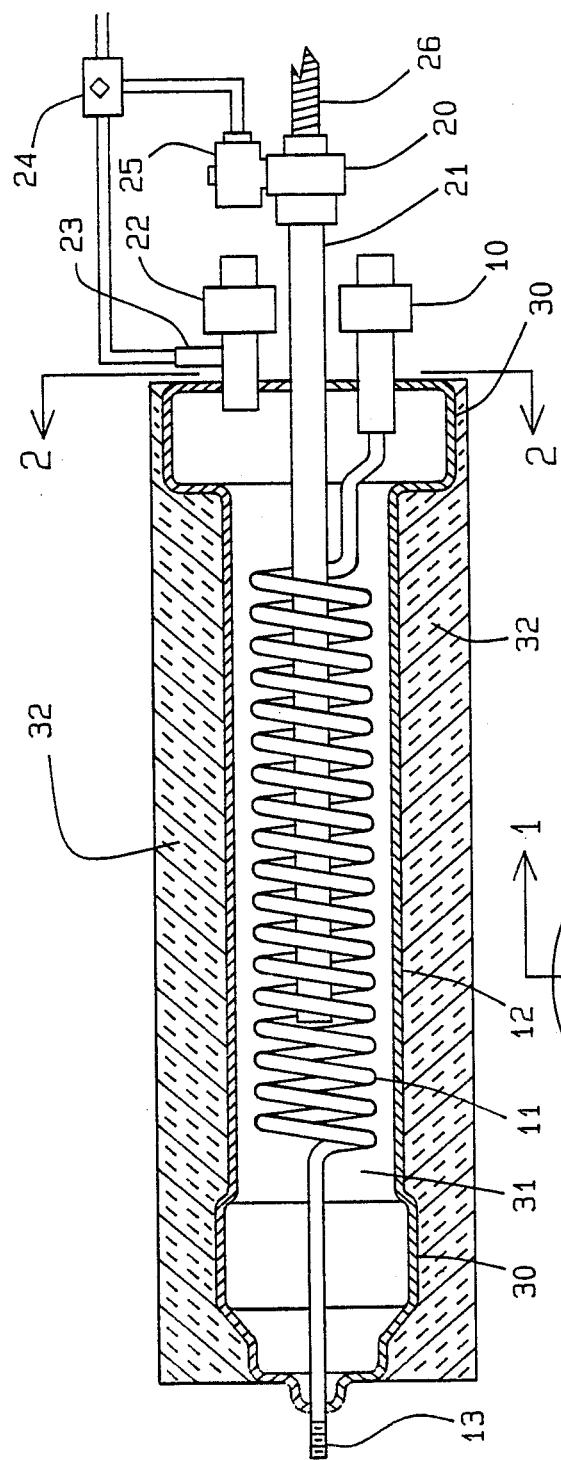
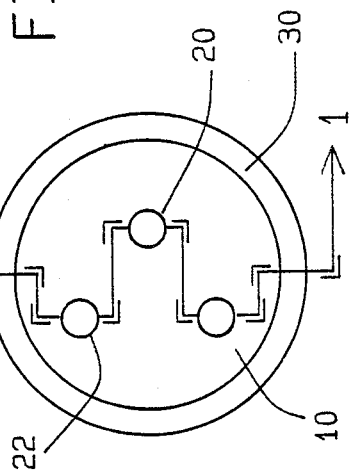
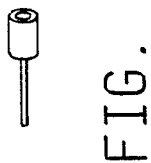
FIG. 1
FIG. 2
FIG. 3

LOW TEMPERATURE CRYOPROBE

CONTRACTUAL ORIGIN OF THE INVENTION

The United States Government has rights in this invention pursuant to Contract No. W-31-109-ENG-38 between the U.S. Department of Energy and the University of Chicago.

BACKGROUND OF THE INVENTION

This invention relates to a low temperature cryoprobe and more particularly to a portable, hand held probe usable within a small confine to produce a point source of gas at a relatively constant temperature of 77 degrees Kelvin.

The metallurgic and semi-conductor industries, among others, use apparatus which must perform in cryogenic temperatures, that is, below 80 degrees Kelvin. Pumps, refrigerators, electrical circuits, electronic circuit boards and other equipment are required to perform within an abnormally cold environment.

As is well known, extreme cold changes the properties of materials, and operators often discover that malfunctions of equipment cannot be duplicated and the causes of malfunctions cannot be isolated when equipment is returned to room temperature. For example, epoxy seals, wire joints, carbon resistors, germanium resistance thermometers, and thermocouple junctions may open only during a cooling cycle of operation.

The terms "cryoprobe" and "cryogenic probe" have been used in the prior art to describe a particular type of instrument suited to the needs of the medical industry. The instrument is used to direct gas at cryogenic temperatures toward human and animal tissue, as an adjunct to what is termed "cryosurgery". (See U.S. Pat. Nos. 4,074,717, Feb. 21, 1978, Schulze; 4,236,518, Dec. 2, 1980, Floyd; 4,376,376, Mar. 15, 1983, Gregory.)

In general, these cryosurgical devices fall within one of two categories, namely, those utilizing high pressure gas to produce low temperatures by the Joules-Thompson phenomena and the second utilizing liquid cryogen. Joules-Thompson equipment typically utilizes gas stored at 500 to 600 psi which is expanded to atmospheric pressure in close proximity to tissue to be necrotized. Such equipment requires adequate safeguards to protect the patient and operator against the hazards associated with these high pressures. Cryogenic devices using liquid cryogen typically operate at relatively low pressures of about one atmosphere and can apply a spray of finely divided liquid cryogen directly to the surface to be necrotized. As cryosurgical devices, the liquid cryogen devices are probably superior, in that they are faster, and an adequate supply of cryogen can be stored in a small heat insulated container readily held and manipulated in the operator's hand.

The present invention combines certain methods known in the prior art with a significant additional feature to provide a low temperature cryoprobe that overcomes shortcomings of the prior art.

As is known in the prior art, material to be cooled is placed in contact with a cold refrigerant near its vaporization temperature. Heat is transferred from the material to be cooled to the refrigerant, warming the refrigerant above its vaporization temperature and forming a gas above the liquid. Changes in the refrigerant's pressure, or rate of flow, or the addition of heat will increase the cooling rate of a given refrigerant. (See U.S. Pat. No. 3,628,347, Apr. 13, 1970, Puckett et al.)

A second known method embodiment in the current invention is the placing of a fluid to be cooled within a helical coil, thereby increasing the contact area between the fluid and the refrigerant. (See U.S. Pat. No. 2,223,152, Jan. 8, 1940, Nagin; U.S. Pat. No. 2,241,186, Mar. 16, 1940, Coons; U.S. Pat. No. 3,696,636, Oct. 10, 1972, Mille.)

At least one cryosurgical probe incorporates the above two methods, as well as the use of multiple nozzles, allowing various densities of flow. (See U.S. Pat. No. 4,116,199, Dec. 6, 1976, Bryne.)

None of the devices described are adequate, however, for the needs of the low temperature researcher. Speaking generally, the low temperature researcher needs an instrument that can be directed at materials which are the suspected cause of a malfunction and that can produce a flow of gas that temporarily returns just the suspect materials to low temperature conditions for the purpose of testing continuity and integrity.

To meet this need, the researcher's instrument must meet specific performance standards. First, and most important, the researcher must be assured that the probe gas is at a constant temperature, eliminating variations in temperature as causes for variation in equipment performance. It is not sufficient that the probe gas exits below 32 degrees fahrenheit, or even zero degrees fahrenheit, as with most cryosurgical probes. It is not sufficient that the temperature of the probe gas was 77 degrees Kelvin when it left the vapor bath if the bath is located remotely, allowing the probe gas to warm substantially by the time it exits the cryoprobe. To meet the low temperature researcher's needs, the temperature of the probe gas when it exits the cryoprobe must be precisely known and controlled.

In addition, the low temperature researcher must be able to use helium as a probe gas in his cryoprobe. Nitrogen is easily sustained at low temperatures and is thus desirable for use in cryosurgical probes. But, nitrogen is the major component of air, making it difficult to detect the presence of nitrogen test gas in a normal laboratory environment. On the other hand, helium introduced to detect leaks in joints and seals will be detectable in small amounts using a helium sensitive mass spectrometer leak detector—an instrument widely used in the industry.

Further, the low temperature researcher must be able to direct a probe gas with precision. Laboratory concerns for low thermal conductivity and minimized heat leak often require that electrical leads be the size of a human hair. The researcher must be able to isolate these leads and other minute details of construction with an equally precise flow.

Finally, the low temperature researcher must be able to sustain the flow of probe gas for extended periods of time, and the cryoprobe must continue to function, despite the fact that the cryoprobe device itself becomes extremely cold.

It is an object of this invention to provide an improved cryoprobe which maintains a flow of cryogen at substantially 77 degrees Kelvin with an accuracy of plus or minus two degrees.

It is another object of this invention to provide an improved cryoprobe which directs a flow of cryogen from a point source, and can therefore be directed with precision.

It is another object of this invention to provide an improved cryoprobe which draws upon a virtually unlimited source of cryogen, thereby insuring operation for a substantially unlimited duration.

It is another object of this invention to provide an improved cryoprobe which uses no mechanical functions, and is not subject, therefore, to breakdown of mechanical functions due to sustained cold.

It is another object of this invention to provide an improved cryoprobe which can use helium gas as its cryogen or probe gas, making it compatible with helium gas detectors commonly found in the industry.

Additional objects, advantages and novel features of the invention will become apparent to those skilled in the art upon examination of the following and by practice of the invention.

SUMMARY OF THE INVENTION

To achieve the foregoing and other objects, this invention comprises a novel improved cryoprobe used to expose equipment to cryogenic temperatures and to produce a source of extreme cold which is easily focused and manipulated. The improved cryoprobe comprises a device having a chamber through which flows liquid nitrogen at 77 degrees Kelvin. Passing through the device and the inside of the chamber is a conduit, shaped in part as a helical coil, through which flows the probe gas—nitrogen or helium. The probe gas is reduced to a temperature of 77 degrees Kelvin by thermal contact with a fluid inside the chamber, and then exits the conduit through an opening adaptable for a number of purposes.

BRIEF DESCRIPTION OF THE DRAWINGS

The present invention is illustrated in the accompanying drawings where:

FIG. 1 shows a section of the improved cryoprobe herein described.

FIG. 2 is a cross section of FIG. 1.

FIG. 3 is a needle attachment used to direct the exiting probe gas.

DETAILED DESCRIPTION OF THE INVENTION

Referring to the drawings, FIG. 1 shows a section of the improved cryoprobe. A stainless steel case 12 is joined with copper end pieces 30 to form a hollow chamber 31. Liquid nitrogen proceeds through an inlet 20, comprised of a one-quarter inch UCRL fitting, and tubing 21 comprised of one-quarter inch stainless steel TW. The liquid nitrogen fills the chamber 31, and as it warms passes to a gaseous phase. The nitrogen exits, preferably as a gas, through an outlet 22, comprised of a one-quarter inch UCRL filling. Rubber tubing (not shown) connected to the outlet 22 disposes of the gas in an open dewar (not shown).

A probe gas such as nitrogen, or alternatively helium, enters at room temperature and a pressure of 4–6 psi, through an inlet 10—a one-quarter inch UCRL fitting—and flows through a conduit 11, comprised of one-eighth inch o.d. copper tubing. The conduit 11 is shaped in part as a helical coil within chamber 31, providing significant thermal contact between the probe gas and the cryogenic nitrogen in the chamber 31. The probe gas is cooled to substantially 77 degrees Kelvin by thermal contact.

Placement of the inlet openings in the copper end 30 is depicted in FIG. 2, a cross section of FIG. 1. Looking at the inlet end of the cryoprobe, the probe gas inlet 10, liquid nitrogen inlet 20 and outlet 22 are spaced appropriately in the copper end piece 30.

The cooled probe gas proceeds through the conduit 11 to an outlet 13, which is threaded with 6–32 thread, permitting the use of any of several attachments with corresponding complementary threads. The attachments may allow dispersion of the probe gas, as with a spray, or they may comprise needles of various sizes, permitting precision focus of a cold gas stream. One such needle attachment is depicted in FIG. 3.

Surrounding the case 12, chamber 31 and the conduit 11 is a layer of Armstrong insulation 32, of size and weight suitable for holding and manipulating by hand. Heat loss between the supply source and the liquid nitrogen inlet 20 is lessened by an insulated metal hose 26.

Despite insulation, however, heat loss will occur, and a relatively constant temperature of 77 degrees Kelvin can only be maintained by appropriate adjustments in the rate of flow of the liquid nitrogen. Because nitrogen changes phase from liquid to gas at 77 degrees Kelvin, the temperature of the nitrogen can be maintained relatively constant at 77 degrees Kelvin by simple observation and adjustment of the rate of flow. The flow of nitrogen can be adjusted by means of a standard cryogenic diaphragm valve (not shown), so that the nitrogen emerges through outlet 22 as a gas, and only a slight adjustment slowing the flow would allow the nitrogen to emerge as a liquid.

Alternatively, as depicted in the preferred embodiment, the temperature of the nitrogen is controlled within plus or minus two degrees of 77 degrees Kelvin by placing a temperature sensing device, such as a diode 23 known to the prior art, in the exit stream of outlet 22. The diode 23 is then connected electrically to a bridge and relay control 24, known to the prior art, which controls a solenoid valve 25, also known to the prior art, in the nitrogen supply line at the liquid nitrogen inlet 20. The bridge and relay control 24 may be adjusted as in the preferred embodiment so that the solenoid valve 25 opens when the temperature at the outlet 22 rises more than a predetermined amount above 77 degrees Kelvin, increasing the rate of flow of liquid nitrogen, and conversely so that the valve 25 closes when the temperature at the outlet 22 drops more than a predetermined amount below 77 degrees Kelvin, decreasing the rate of flow of liquid nitrogen. Thus the temperature of the liquid nitrogen and of the probe gas it cools is maintained at 77 degrees Kelvin within plus or minus two degrees.

The duration of flow of both the liquid nitrogen and the probe gas is dependent upon the size of the supply. Coupling with a central source or a very large dewar provides a virtually unlimited supply.

The embodiment of the invention in which an exclusive property or privilege is claimed is defined as follows:

1. A portable, hand held cryoprobe comprised of:
   a casing having a hollow chamber with an inlet and an outlet for the introduction, retention and passage of nitrogen,
   means to control the flow of nitrogen through said hollow chamber, so that the nitrogen proceeds from an inlet into the chamber and to an outlet, entering as a liquid and exiting as a gas, conduit means within and extending through said casing and hollow chamber, configured in part as a helical coil, a probe gas proceeding from an inlet through said conduit means to an outlet with attachment means.

2. An apparatus as defined in claim 1 wherein said probe gas is nitrogen.

3. An apparatus as defined in claim 1 wherein said probe gas is helium.

4. An apparatus as defined in claim 1 wherein said means to control the flow of nitrogen comprises a solenoid valve.

5. An apparatus as defined in claim 4 comprising temperature sensing means for controlling said solenoid valve.

6. An apparatus as defined in claim 5 wherein said temperature sensing means comprises a diode in the exit stream of said nitrogen outlet.

7. An apparatus as defined in claim 1 wherein said attachment means comprises a 6-32 thread.

8. An apparatus as defined in claim 1 wherein said attachment means comprises a needle.

9. An apparatus as defined in claim 1 including insulation means enclosing said casing, chamber and conduit means.

* * * * *